United States Patent
Reydel et al.

(12) United States Patent (10) Patent No.: US 9,433,747 B2
Reydel et al. (45) Date of Patent: Sep. 6, 2016

(54) TWIST-IN SPRING-SKIRT-LIKE SPHINCTEROTOME

(71) Applicant: Inventio LLC, West Caldwell, NJ (US)

(72) Inventors: Boris Reydel, West Caldwell, NJ (US); Ben Reydel, West Caldwell, NJ (US)

(73) Assignee: Inventio LLC, West Caldwell, NJ (US)

( * ) Notice: Subject to any disclaimer, the term of this patent is extended or adjusted under 35 U.S.C. 154(b) by 945 days.

(21) Appl. No.: 13/623,260

(22) Filed: Sep. 20, 2012

(65) Prior Publication Data

US 2013/0023854 A1 Jan. 24, 2013

Related U.S. Application Data

(63) Continuation-in-part of application No. 11/883,300, filed as application No. PCT/US2006/001136 on Jan. 13, 2006, now Pat. No. 8,366,673.

(60) Provisional application No. 60/649,101, filed on Feb. 3, 2005, provisional application No. 61/626,099, filed on Sep. 21, 2011.

(51) Int. Cl.
| | | |
|---|---|---|
| *A61M 25/00* | (2006.01) | |
| *A61B 17/22* | (2006.01) | |
| *A61B 17/221* | (2006.01) | |
| *A61B 17/00* | (2006.01) | |
| *A61B 17/30* | (2006.01) | |

(52) U.S. Cl.
CPC .......... *A61M 25/003* (2013.01); *A61B 17/221* (2013.01); *A61B 17/22031* (2013.01); *A61M 25/007* (2013.01); *A61M 25/0074* (2013.01); *A61B 2017/00349* (2013.01); *A61B 2017/2212* (2013.01); *A61B 2017/22034* (2013.01); *A61B 2017/306* (2013.01); *A61M 25/0082* (2013.01)

(58) Field of Classification Search
CPC .................. A61B 17/221; A61B 2017/22034; A61B 2017/2212; A61B 2017/2215; A61B 2017/2217; A61F 2202/016; A61M 25/0074; A61M 25/0082
See application file for complete search history.

(56) References Cited

U.S. PATENT DOCUMENTS

| | | | |
|---|---|---|---|
| 5,192,286 A | 3/1993 | Phan et al. | |
| 6,436,112 B2 * | 8/2002 | Wensel | 606/127 |
| 2001/0044595 A1 | 11/2001 | Reydel et al. | |

(Continued)

FOREIGN PATENT DOCUMENTS

| | | |
|---|---|---|
| AU | 2006203116 A1 | 7/2006 |
| WO | WO 2010/087330 A1 | 8/2010 |

OTHER PUBLICATIONS

Notification of Transmittal of the International Search Report and the Written Opinion of the International Searching Authority, or the Declaration, dated Jan. 3, 2013, for corresponding application No. PCT/US2012/056212, 5p.

*Primary Examiner* — Kami A Bosworth
(74) *Attorney, Agent, or Firm* — Meunier Carlin & Curfman LLC

(57) ABSTRACT

A system and method for gaining access to an internal bodily structure, such as the ampullae. The system includes an elongate catheter having a lumen extending there through. An elongate wire including a distal coil is movably extendable from the distal end of the catheter and is configured to engage the inner surface of the bodily structure. Proximal movement of the elongate wire flattens the inner surface of the bodily structure and aligns the passageway thereof with the longitudinal axis of the catheter.

17 Claims, 17 Drawing Sheets

(56) References Cited

U.S. PATENT DOCUMENTS

| | | | |
|---|---|---|---|
| 2002/0133190 A1* | 9/2002 | Horton | A61B 17/12118 606/194 |
| 2003/0078473 A1 | 4/2003 | Richardson | |
| 2004/0073243 A1* | 4/2004 | Sepetka | A61B 17/22031 606/159 |
| 2006/0173422 A1 | 8/2006 | Reydel et al. | |
| 2007/0260158 A1 | 11/2007 | McLaren | |
| 2008/0287961 A1 | 11/2008 | Miyamoto et al. | |
| 2008/0306467 A1 | 12/2008 | Reydel | |
| 2009/0043259 A1 | 2/2009 | Hardin, Jr. et al. | |
| 2011/0028833 A1 | 2/2011 | Pasricha | |

* cited by examiner

Fig. 11A
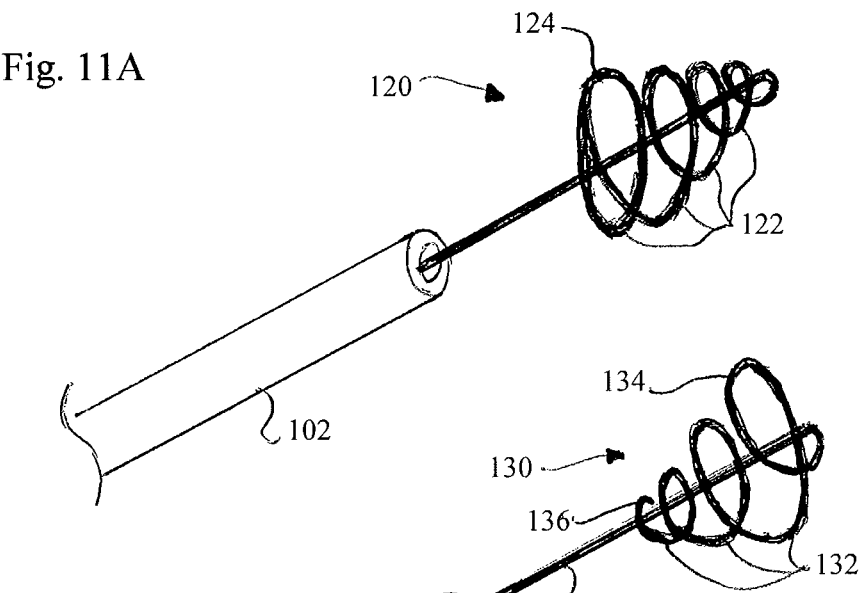
Fig. 11B
Fig. 11C
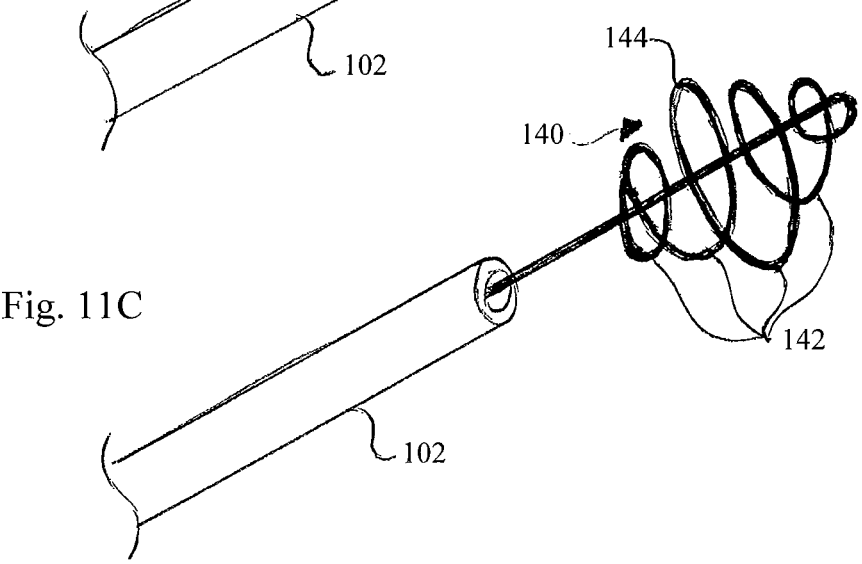

TWIST-IN SPRING-SKIRT-LIKE SPHINCTEROTOME

RELATED APPLICATIONS

This application is a continuation-in-part of U.S. Pat. No. 8,366,673, filed Feb. 1, 2008, titled "Method and Devices for Selective Endoscopic Retrograde Cholangiopancreatography", which is a U.S. Nationalization of PCT Application No. PCT/US06/01136, filed Jan. 13, 2006, and which claims the benefit of U.S. Provisional Application No. 60/649,101, filed Feb. 3, 2005, the contents of which are incorporated herein by reference. This application also claims the benefit of priority from U.S. Provisional Application No. 61/626,099, filed Sep. 21, 2011, and titled "Screw-In Method and Devices for ERCP", the contents of which is incorporated herein by reference.

TECHNICAL FIELD

The present disclosure relates to endoscopic retrograde cholangiopancreatography and, more specifically, to methods and devices for selective endoscopic retrograde cholangiopancreatography.

BACKGROUND

Endoscopic retrograde cholangiopancreatography (ERCP) is the visualization of the pancreatic and biliary ducts by means of endoscopic injection of a contrast medium through the hepatopancreatic ampulla (the ampulla of Vater). A retrograde image of both structures can be formed on an X-ray. ERCP may be used to facilitate the diagnosis of obstructions, for example, gallstones or cholangiocarcinoma.

In performing ERCP, an endoscope or catheter may be inserted through the mouth of the patient, down the esophagus, through the stomach, through the pylorus into the duodenum to the ampulla. A catheter or cannulatome may be inserted through the lumen of the endoscope or catheter to the ampulla to deliver radiocontrast into the bile ducts and/or pancreatic duct. The structures receiving radiocontrast may then be visualized by X-ray imaging techniques such as fluoroscopy.

Devices such as a catheter, guidewire, papillotome, etc. may be sent through the lumen of the endoscope or catheter for purposes such as radiocontrast delivery, specimen biopsy, etc. These devices may become obstructed by folds of the mucosa inside the ampullae that are either natural or an effect of the endoscope and/or its device's wrinkling of the mucosa as it is inserted into the ampullae. Similar folding may occur in the intramural portion of the common bile duct (CBD) and/or pancreatic duct.

FIG. 1 is a diagram illustrating endoscope/catheter redundant mucosa fold obstruction. As an endoscope or medical catheter 10 is inserted into the ampullae 11, the CBD 13 and/or the pancreatic duct 14, folds 12 within the inner-lining of the structures may form. These folds 12 may obstruct the endoscope or medical catheter 10 and/or an elongate device such as a guidewire, papillotome, etc. that may be inserted through the endoscope or catheter 10.

As these folds may complicate ERCP, it is desirable to use a method and device for straightening out folds within the ampullae, bile ducts and/or pancreatic duct when performing ERCP. It is also desirable to use a method and device for aligning the bodily passageway of the ampullae, bile ducts and/or pancreatic duct with the longitudinal axis of the device so as to facilitate access through the desired bodily passageway.

BRIEF SUMMARY

A catheter for inserting into a bodily structure. The catheter includes a primary lumen for passing a device. One or more flaps or circumferential anchors protrude from a front tip of the catheter. The flaps or circumferential anchors engage with an inter-mural mucosa of the bodily structure.

A catheter for inserting into a bodily structure includes a primary lumen for passing a device and one or more secondary lumens with negative pressure for engaging with an inter-mural mucosa of the bodily structure.

A system for inserting into a bodily structure includes an elongate catheter and a coiled engagement member movably disposed therein. The coiled engagement member includes a coil for engaging with an inter-mural mucosa of the bodily structure.

A method for inserting a catheter into a bodily structure includes inserting a catheter with one or more flaps or circumferential anchors protruding from a front tip of the catheter into the bodily structure. The catheter is pulled back to engage the one or more flaps or circumferential anchors with an inter-mural mucosa of the bodily structure. The inter-mural mucosa is thereby pulled taut and/or to align the passageway of the bodily structure with the catheter. A device is then inserted through a primary lumen of the catheter and into the bodily structure.

A method for inserting a catheter into a bodily structure includes inserting a catheter into the bodily structure. One or more points of negative pressure on the catheter are activated to engage an inter-mural mucosa of the bodily structure. The catheter is pulled back to pull the inter-mural mucosa taut and/or to align the passageway of the bodily structure is aligned with the catheter. A device is then inserted through a primary lumen of the catheter and into the bodily structure.

A method for inserting a catheter into a bodily structure includes inserting a system comprising a catheter and a coiled engagement member into the bodily structure. The coiled engagement member includes a coil that is rotated to engage an inter-mural mucosa of the bodily structure. The coiled engagement member is pulled back to pull the inter-mural mucosa taut and/or to align the passageway of the bodily structure with the catheter. A device is then inserted through a primary lumen of the catheter and into the bodily structure.

BRIEF DESCRIPTION OF THE SEVERAL VIEWS OF THE DRAWINGS

A more complete appreciation of the present disclosure and many of the attendant advantages thereof will be readily obtained as the same becomes better understood by reference to the following detailed description when considered in connection with the accompanying drawings, wherein:

FIGS. 11A-11C show alternative embodiments of a coiled member having variable profiles according to the present invention;

DETAILED DESCRIPTION OF PRESENTLY PREFERRED EMBODIMENTS

Figure 1:
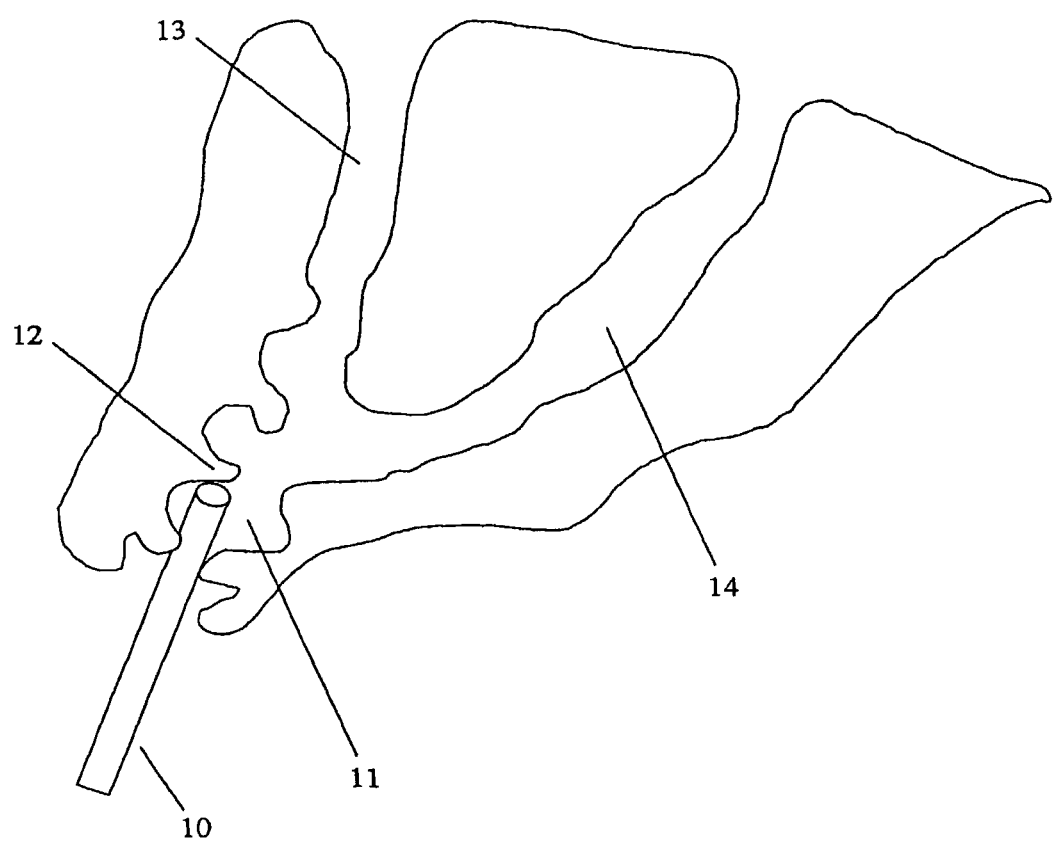
FIG. 1 is a diagram illustrating endoscope/catheter redundant mucosa fold obstruction.

In describing the preferred embodiments of the present disclosure illustrated in the drawings, specific terminology is employed for sake of clarity. However, the present disclosure is not intended to be limited to the specific terminology so selected, and it is to be understood that each specific element includes all technical equivalents which operate in a similar manner.

Embodiments of the present invention seek to straighten out folds within the inner walls of bodily structures, for example, the ampullae, bile ducts and/or pancreatic duct, for example, when performing ERCP. As mentioned above, the folds may be preexisting or may be caused by the insertion of a catheter into the bodily structure. For example, as the catheter is inserted into the bodily structure, the inner walls of the bodily structure may be pushed upwards causing a buckling resulting in the folding of the inner walls of the bodily structure.

Embodiments of the present invention may straighten the folds by pulling the inner surface of the bodily structure, for example, the inter-mural mucosa of the ampullae, bile ducts and/or pancreatic duct, taut and smooth. Insertion if a device such as a catheter, guidewire or papillotome may then be facilitated by the removal of potentially obstructive wrinkles. Embodiments of the present invention may also align the passageway of the bodily structure with the catheter, guidewire of papillotome, thereby facilitating advancement thereof into the bodily structure. For example, ERCP may be performed.

Figure 2:
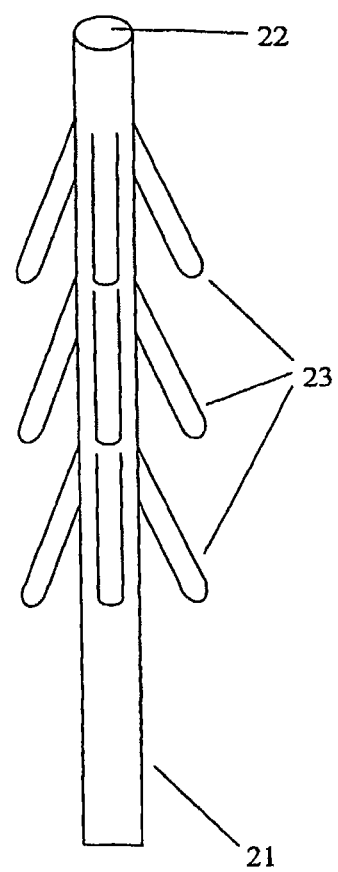
FIG. 2 is a diagram showing a specialized ERCP catheter according to an embodiment of the present invention.

A specialized ERCP catheter may be used to straighten out wrinkles within the inter-mural mucosa of the ampullae, bile ducts and/or pancreatic duct. FIG. 2 is a diagram showing a specialized ERCP catheter according to an embodiment of the present invention. The specialized ERCP catheter 21 may have a tip opening 22 for protrusion of a device such as a catheter, guidewire, papillotome, or contrast injection. The front tip of the catheter 21 may have one or more rows of flaps or petals 23 (referred to herein as flaps) around the perimeter of the catheter. There may be a number of rows of flaps 23. For example, there may be 1, 2, or three rows of flaps 23. Each row of flaps 23 may have a number of flaps 23, for example, each row may have 1, 2, 3 or 4 flaps 23. The flaps 23 may have flat and/or blunt ends for engaging the redundant mucosa, for example, within the ampullae. After the catheter 21 is at least partially inserted into, for example, the ampullae, the catheter 21 may then be gently pulled back. As the catheter 21 is pulled back, the flaps 23 engage with the redundant mucosa and may pull the inner surface of the ampullae taut and smooth, thereby minimizing the number and size of wrinkles within the intra-mural mucosa that may potentially obstruct the catheter and/or the protruding device.

According to one embodiment of the present invention, the flaps may be incomplete, meaning that the flaps are shaped to push into the thickness of the inter-mural mucosa without cutting into the internal lumen of the bodily structure, for example, the ampullae. According to another embodiment of the present invention, the flaps may be complete, meaning that the flaps are shaped to cut into the internal lumen of the bodily structure.

Figure 3:
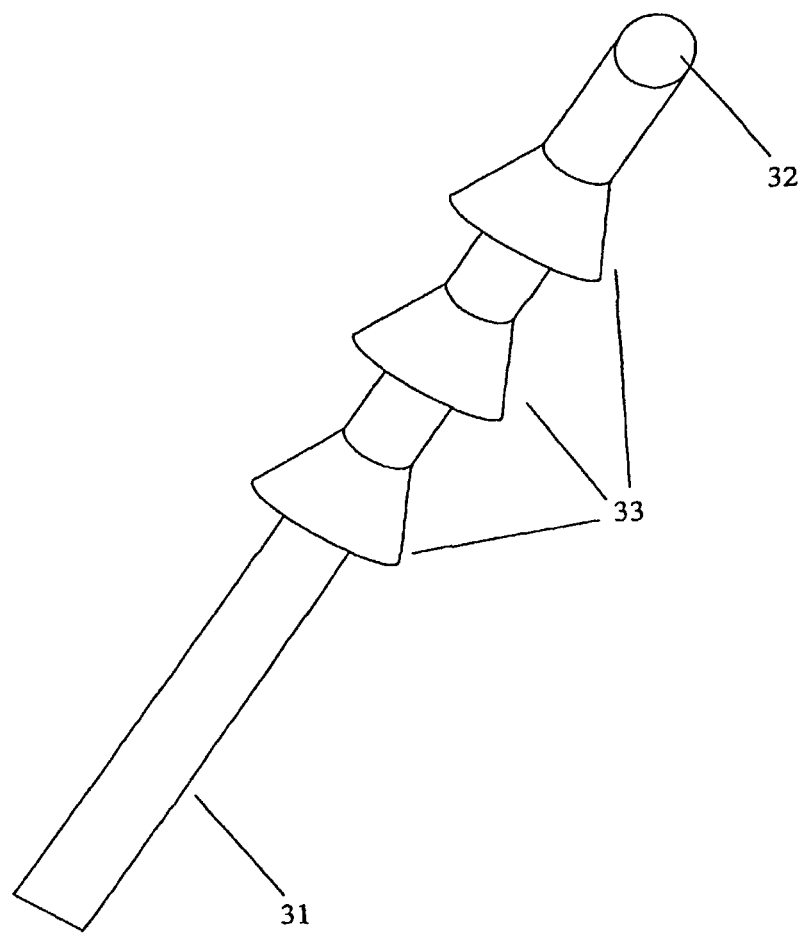
FIG. 3 is a diagram showing a specialized ERCP catheter with complete flaps according to an embodiment of the present invention.

Embodiments of the present invention may use circumferential anchors rather than or in addition to flaps. FIG. 3 is a diagram showing a specialized ERCP catheter with circumferential anchors according to an embodiment of the present invention. The catheter 31 may have a top opening 32 for protrusion of a device such as a catheter, guidewire, papillotome, or contrast injection. The front tip of the catheter 31 may have one or more circumferential anchors 33 around the perimeter of the catheter 31. The circumferential anchors 33 may extend 360 degrees around the entire circumference of the catheter 31. For example, there may be 1, 2 or 3 circumferential anchors 33. The circumferential anchors 33 may either be fully enclosed raised cone or may be thin and without volume. The circumferential anchors 33 may have flat and/or blunt ends for engaging the redundant mucosa, for example, within the ampullae. After the catheter 31 is at least partially inserted into, for example, the ampullae, the catheter 31 may then be gently pulled back. As the catheter 31 is pulled back, the circumferential anchors 33 engage with the redundant mucosa and may pull the inner surface of the ampullae taut and smooth thereby minimizing the number and size of the wrinkles.

Figure 4A:
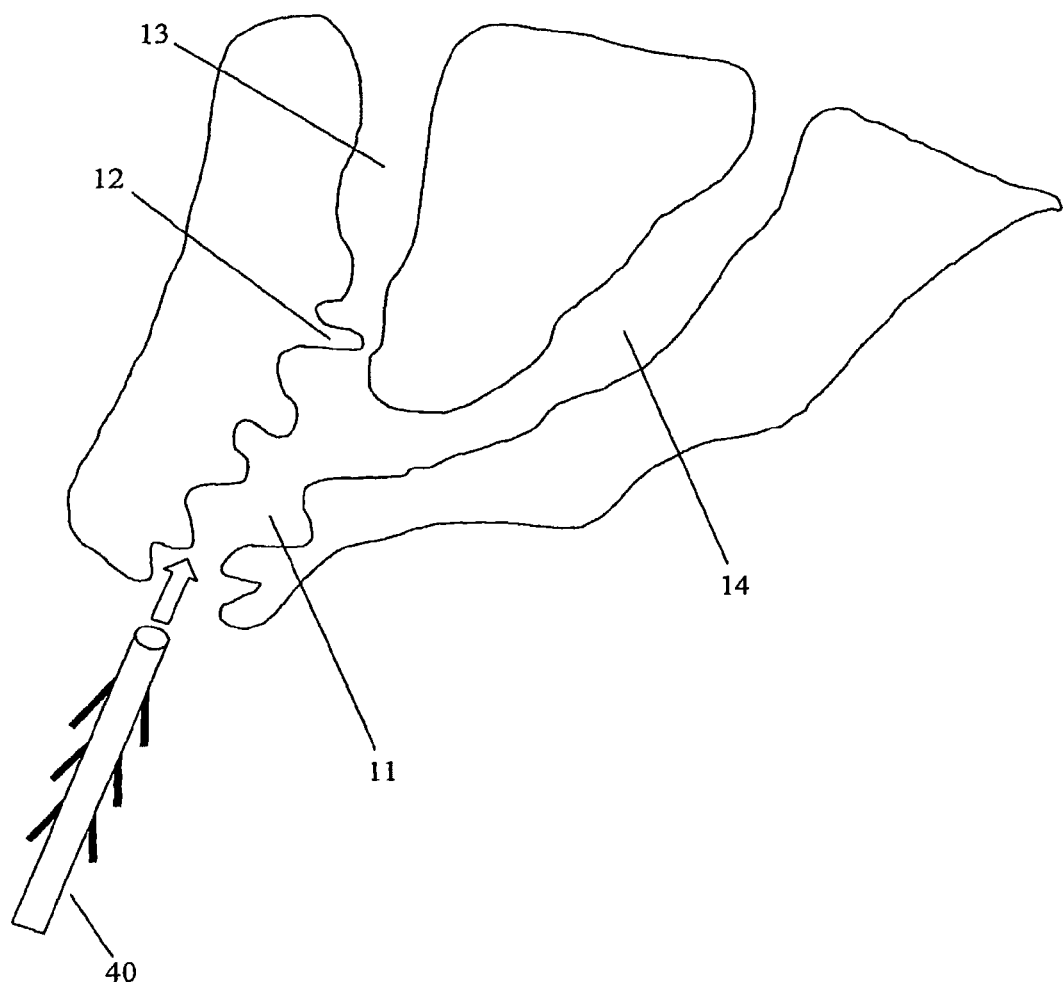
FIGS. 4A, 4B, and 4C show a method for using a specialized catheter to straighten out wrinkles within the inter-mural mucosa of the ampullae, bile ducts and/or pancreatic duct according to an embodiment of the present invention.
Figure 4B:
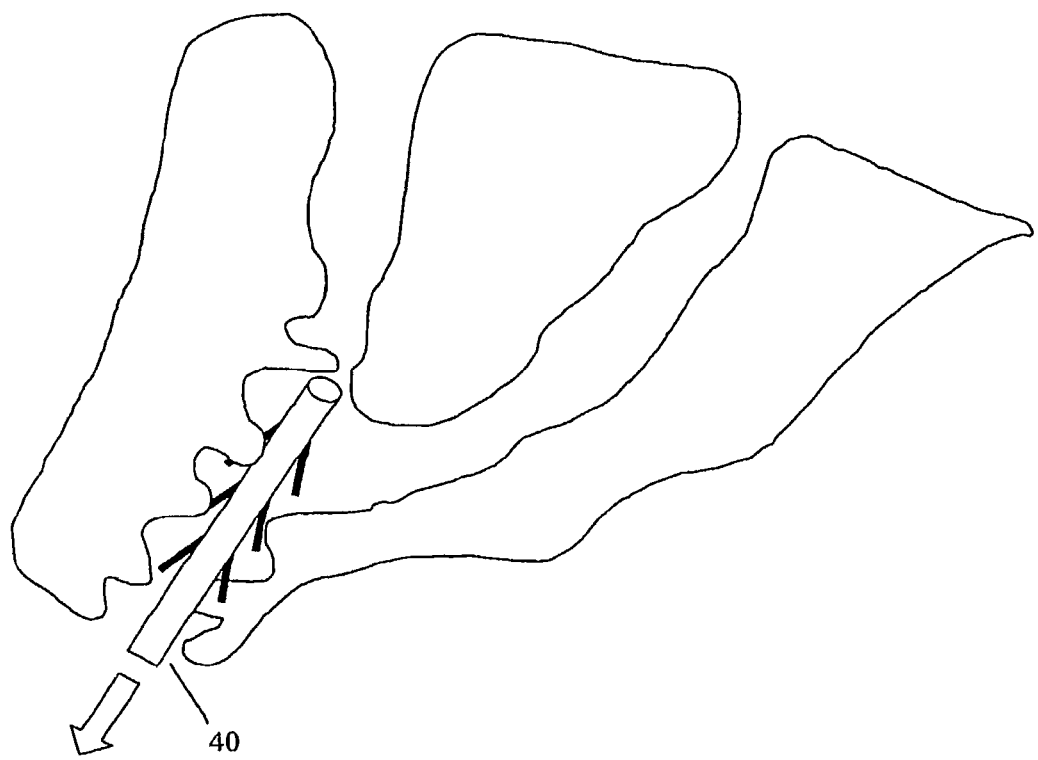
Figure 4C:
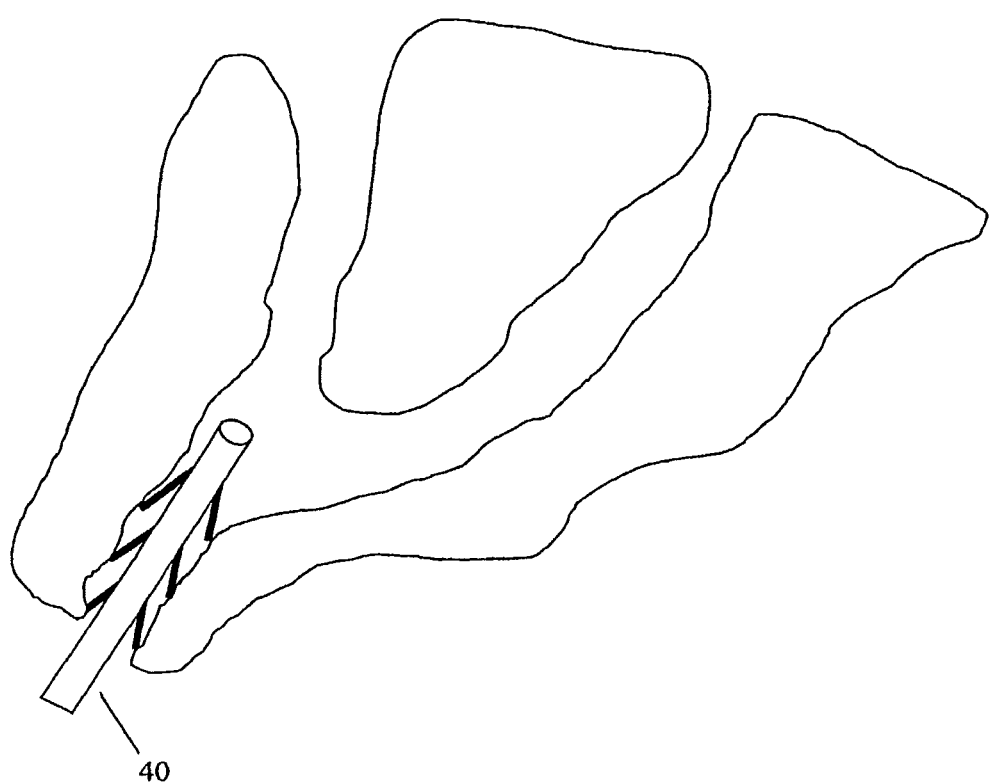

FIGS. 4A, 4B, and 4C show a method for using a specialized catheter to straighten out wrinkles within the inter-mural mucosa of the ampullae, bile ducts and/or pancreatic duct according to an embodiment of the present invention. Referring to FIG. 4A, the specialized catheter 40 may be inserted into, for example, the ampullae 11, the CBD 13 and/or the pancreatic duct 14. As the catheter 40 is inserted, folds 12 may develop or appear in the inter-mural surface of the structure.

FIG. 4B shows the catheter 40 at least partially inserted into the ampullae 11. For example, the tip of the catheter 40 may be inserted 2-5 mm into the ampullary orifice. Once the catheter 40 has been inserted, the catheter may be gently pulled back. The blunt ends of the catheter's flaps and/or circumferential anchors may engage the redundant mucosa inside the ampullae. The flaps and/or circumferential anchors may then function as gentle hooks or anchors around the perimeter of the tip of the catheter to taut and straighten the redundant mucosa more distal to the flaps and/or circumferential anchors.

The pulling motion may minimize the number and size of the folds and may thereby minimize obstruction of the ampullae as illustrated in FIG. 4C. By straightening the ampullae, folding may also be reduced in the CBD and/or the pancreatic duct. After the structures have been straightened, a guidewire may be advanced through the catheter and/or a contrast may be injected. Thus, the tip of the guidewire tip could straighten the passageway or lumen of the structure and more easily travel through the structure without getting stuck on a wrinkle.

The number and position of the flaps and/or circumferential anchors around the catheter's tip's perimeter may be varied to achieve the desired degree to which the lumen of the structure is opened. For example, a flap placed at the 11 o'clock orientation may make a biliary cannulation more plausible while a flap placed at the 3 o'clock orientation make a pancreatic cannulation more plausible.

The catheter itself may be single-, two-, or three-channeled for simultaneous use with wires and contrast. The flaps and/or circumferential anchors of the present invention may also be applied to papillotomes or other catheter devices. Likewise, the flaps and/or circumferential anchors may be applied to endoscopes or other introducer devices.

Figure 5A:
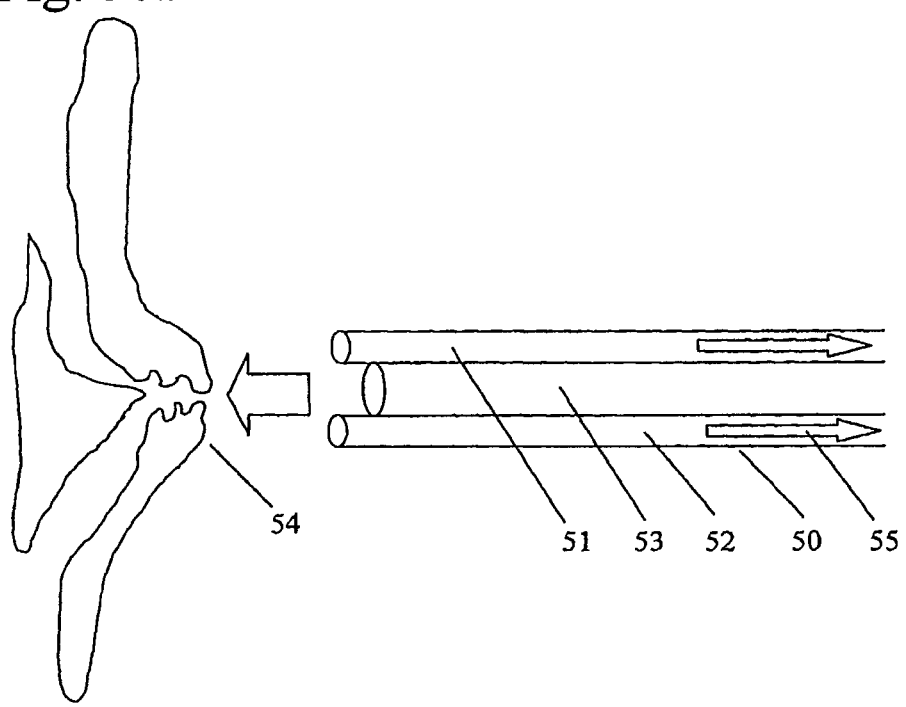
FIGS. 5A and 5B show a specialized catheter according to such an embodiment of the present invention.
Figure 5B:
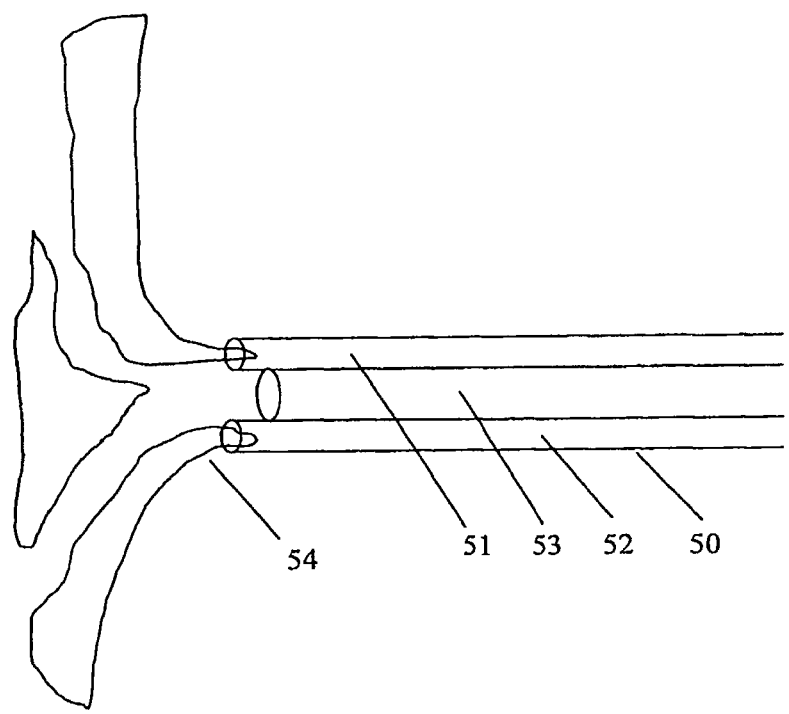

Other embodiments of the present invention may minimize mucosal folds by engaging the rim of the ampullae and pulling it out and open while a thinner catheter and/or guidewire is passed through the taut internal canal. FIGS. 5A and 5B show a specialized catheter according to such an embodiment of the present invention. FIG. 5A shows the specialized catheter 50 approaching the ampullae 54. The catheter 50 may contain an inner passageway or lumen 53 and one or more suction channels 51 and 52. For example, there may be two suction channels 51 and 52 positioned at 9 and 3 o'clock, or at 11 o'clock for selective bile duct cannulation. The suction channels 51 and 52 may deliver negative pressure suction 55 to create points of negative pressure at the tips of the suction channels 51 and 52. As the catheter 50 approaches the ampullae 54, the rim of the ampullae 54 may be pulled into the suction channels 51 and 52 by the negative pressure suction 55, as seen in FIG. 5B. This pulling of the rim of the ampullae 54 may pull the redundant mucosa taut thereby minimizing wrinkles. A device, for example a catheter, guidewire, papillotome, or contrast injection may then be sent through the inner lumen 53 of the catheter 50, for example, to perform ERCP. Afterwards, the suction 55 may be discontinued to release the ampullae 54 to facilitate removal of the catheter 50. To minimize the risk of undesired engagement of the mucosa, the suction may be inactive during insertion of catheter 50.

Figure 6:
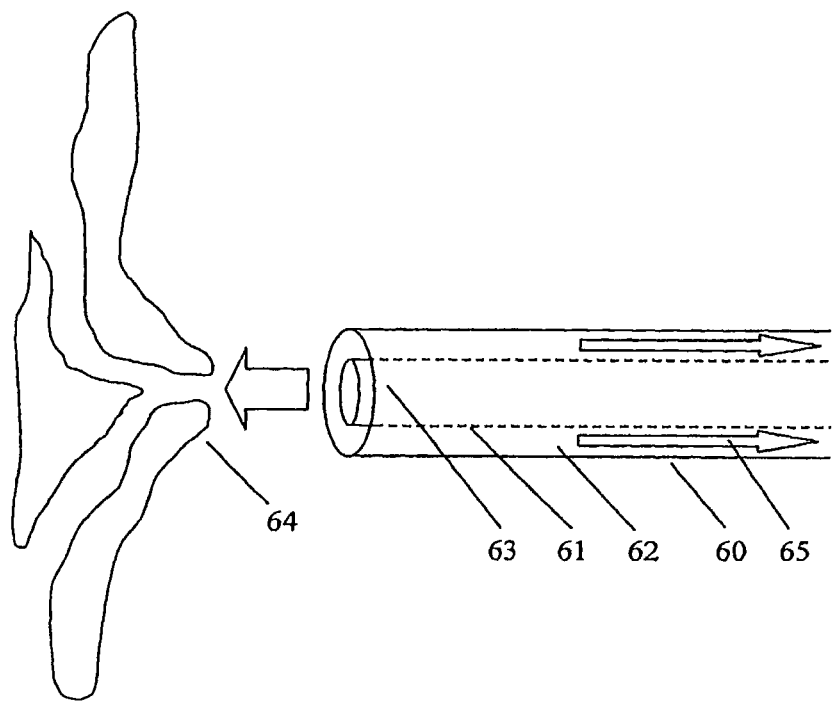
FIG. 6 shows a double-walled catheter that may be used according to an embodiment of the present invention.

According to another embodiment of the present invention, a double-walled catheter may be used. An example of such an embodiment is shown in FIG. 6. Here, a double-walled catheter 60 includes an outer passageway 62 and an inner passageway 63 separated by an inner catheter 61. Negative pressure suction 65 may be applied to the outer passageway 62 to create a point of negative pressure at the tip of the outer passageway 62 so that as the catheter 60 approaches the ampullae 64, the entire perimeter or rim of the ampullae 64 may be pulled into the outer passageway 62 by the negative pressure suction 65. This pulling of the perimeter of the ampullae 64 may pull the redundant mucosa taut thereby minimizing obscuring wrinkles. A device, for example, a catheter, guidewire, papillotome, or contrast injection may then be sent through the inner passageway 63 of the catheter 60, for example, to perform ERCP. Afterwards, the suction 65 may be discontinued to release the ampullae 64 to facilitate removal of the catheter 60. To minimize the risk of undesired engagement of the mucosa, the suction may be inactive during insertion of catheter 60.

Figure 7:
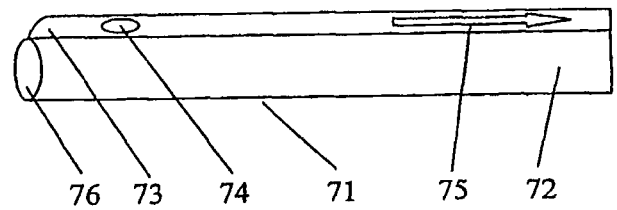
FIG. 7 shows a double-lumen catheter that may be used according to an embodiment of the present invention.

According to another embodiment of the present invention, a double-lumen catheter may be used. An example of such an embodiment is shown in FIG. 7. Here, a double-lumen catheter 71 includes a primary lumen 72 and a secondary lumen 73. Negative pressure suction 75 may be applied to the secondary lumen 73. The secondary lumen may have a single side hole 74 for attaching to the lining inside the orifice at a single point by the force of the suction 75, this single side hole 74 acting as a point of negative pressure. Once the side hole 74 has attached to the lining, the catheter 71 may be pulled back to straighten the redundant mucosa and minimize obstructive wrinkles. A device, for example, a catheter, guidewire, papillotome, or contrast injection may then be sent through the primary lumen 72 of the catheter 71 through a front opening 76, for example, to perform ERCP. Afterwards, the suction 75 may be discontinued to release the orifice inner lining to facilitate removal of the catheter 71. To minimize the risk of undesired engagement of the mucosa, the suction may be inactive during insertion of catheter 71.

In embodiments of the present invention that use flaps and/or circumferential anchors (e.g. the embodiments of FIGS. 2 and 3), the flat and/or blunt ends of the flaps and/or circumferential anchors may prevent perforation of the mucosa. Additionally, at sufficient tension, for example, when the catheter is removed, the flaps and/or circumferential anchors should be able to buckle over or collapse to release the mucosa. Removal of the catheter should not cause significant trauma to the mucosa.

Figure 8A:
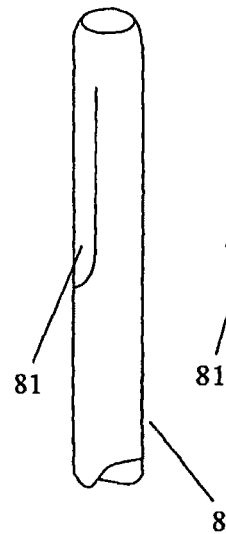
FIGS. 8A-8D show a catheter with a retractable flap according to embodiments of the present invention.
Figure 8B:

Other embodiments of the present invention may facilitate removal of the catheter by utilizing retractable flaps and/or circumferential anchors. FIGS. 8A-8D show examples of catheters with retractable flaps according to embodiments of the present invention. FIG. 8A shows a catheter 80 with a retractable flap 81 in the retracted position. The flap 81 may be retracted for insertion and/or removal of the catheter. FIG. 8B shows a catheter 80 with a retractable flap 81 in the open position. The flap 81 may be open when engaging the redundant mucosa.

Figure 8C:
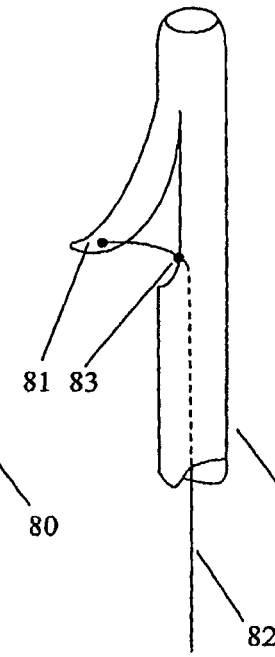
Figure 8D:
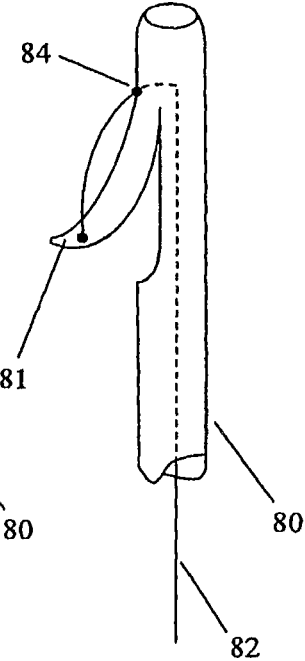

The retractable flap 81 may be biased in either the open position or the closed position. If the flap 81 is biased in the open position, the flap 81 may be pulled closed by a wire 82 that runs the length of the catheter 80 and exits the catheter 80 through a point 83 located behind the flap 81 as shown in FIG. 8C. If the flap 81 is biased in the closed position, the flap 81 may be pulled open by a wire 82 that runs the length of the catheter 80 and exits the catheter 80 through a point 84 above the flap 81 as shown in FIG. 8D. It is to be understood that the catheter 80 may have any number of flap 81 as described above.

Figure 9A:
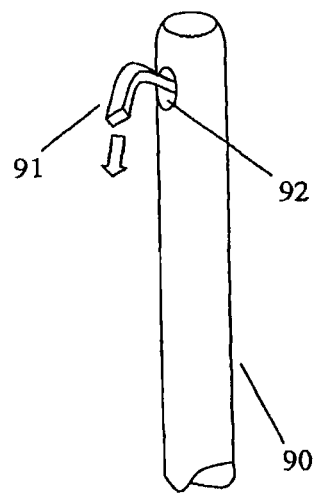
FIGS. 9A and 9B show retractable flaps according to another embodiment of the present invention.
Figure 9B:
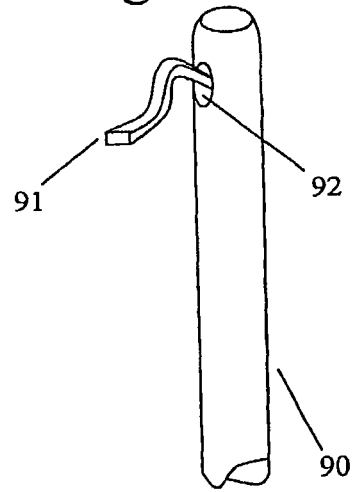

FIGS. 9A and 9B show retractable flaps according to another embodiment of the present invention. The catheter 90 may have a side hole 92. A retractable flap 91 may then be pushed and retracted though the side hole 92 as desired. The retractable flap 91 may be made of a memory-shaped flat wire. FIG. 9A shows such the catheter 90 with a partially extended flap 91 while FIG. 9B shows the catheter 90 with a fully extended flap 91. It is to be understood that the catheter 90 may have any number of flaps 91 as described above.

Embodiments of the present invention may utilize circumferential anchors such as those shown in FIG. 3 that are retractable. Such circumferential anchors may open and close, for example, in an umbrella like fashion.

Figure 10A:
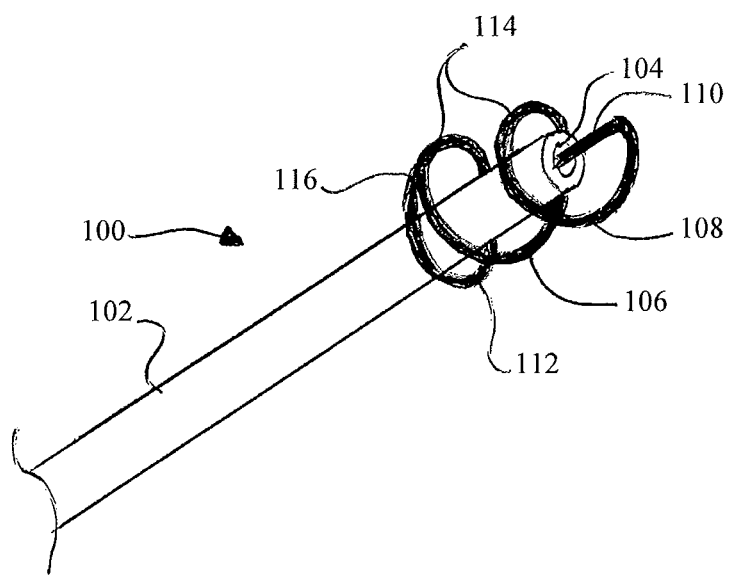
FIGS. 10A and 10B show a system including a catheter and a coiled member according to an embodiment of the present invention.
Figure 10B:
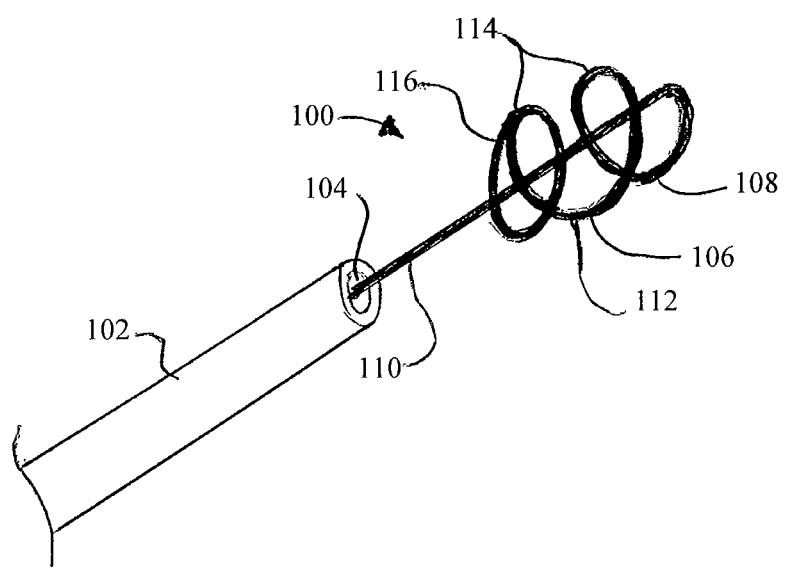

FIGS. 10A and 10B show an alternative system for gaining access to an internal bodily structure in accordance with the present invention. The system 100 includes an elongate medical catheter 102 having a lumen 104 extending longitudinally there through. The system 100 further comprises a coiled engagement member 106, which includes a coil 108 disposed on the distal end of an elongate shaft 110. The shaft 110 is extended through the lumen 104 of the catheter 102 such that the coil 108 is disposed near or about the distal end of the catheter 102. The shaft 110 is rotatable and longitudinally movable within the lumen 104 of the catheter 102 to permit the coil 108 to be advanced, retracted and/or rotated relative to the catheter 102.

The shaft 110 has sufficient torsional rigidity to permit rotational motion applied to the proximal end of the shaft 110 to be transmitted to the coil 108. The shaft 110 also preferably has sufficient longitudinal rigidity to permit axial forces applied to the proximal end of the shaft 110 to be transmitted to the coil 108. In other words, the shaft 110 preferably has sufficient rigidity or stiffness to permit manipulation of the coil 108 via manipulation of the proximal end of the shaft 110. Nevertheless, the shaft 110 should be sufficiently flexible to permit advancement along a tortuous pathway through the bodily lumen of a patient.

As will be explained in greater detail below, the coil 108 is configured to engage the inner surface of the bodily lumen, for example, the inter-mural mucosa of the ampullae. The coil 108 is engaged by first contacting the coil 108 with the inner surface of the bodily lumen, and then rotating the coil 108 so as to advance the coil into the passageway of the ampullae via a screw-in type of action. Once the coil 108 is fully engaged with the inter-mural mucosa of the ampullae, the coiled engagement member 106 can be used to flatten out wrinkles within the inter-mural mucosa of the ampullae, or to align the passageway of the ampullae with the longitudinal axis of the catheter 102.

In the embodiment shown in FIGS. 10A and 10B, the coil 108 comprises a wire 112 that forms a plurality of loops 114 having a generally spiral configuration. The wire 112 is integrally formed with the shaft 110, and curves outwardly and proximally from the distal end of the shaft 110. The wire 112 loops about the shaft 110 in a spiral configuration to form the coil 108. In the particular embodiment illustrated, the wire 112 wraps or loops about the shaft 110 approximately two times so as to form two loops 114, although a fewer or greater number of loops 114 can be utilized. In the particular embodiment illustrated, the loops 114 of the wire 112 have a substantially constant radius relative to the longitudinal axis of the shaft 110. In addition, the radius of the loops 114 is generally large enough to allow the coil 108 to be disposed about the distal end of the catheter 102, as best seen in FIG. 10A. The end 116 of the wire 112 is preferably attached to the proximal-most loop 114 of the coil 108 so as to prevent the end 116 from puncturing or injuring bodily tissue. Attachment of the end 116 to the loop 114 of the coil 108 also stiffens the proximal-most loop 114. Alternatively, the end 116 of the wire may be attached to the shaft 110. In other embodiments, which will be described below, the end 116 of the wire 112 may be unconnected to either the coil 108 or the shaft 110.

As will be explained in greater detail below, the coiled engagement member 106 is configured to engage the inner surface of the bodily lumen, for example, the inter-mural mucosa of the ampullae. The coil 108 is engaged by first contacting the coil 108 with the inner surface of the bodily lumen, and then rotating the coil 108 so as to advance the coil into the passageway of the ampullae via a screw-in type of action. This may be accomplished using a number of different techniques or methods by placing the system 100 in different configurations. FIG. 10A illustrates a first configuration for the system 100 wherein the loops 114 of the coil 108 are disposed circumferentially about the distal end of the catheter 102. This configuration provides lateral support to the coil 108, and prevents the coil 108 from collapsing as it is rotated or screwed into engagement with the inner surface of the bodily lumen. Specifically, the outer surface of the shaft of the catheter 102 acts as a backstop against excessive inward movement of the loops 114 of the coil 108 as the loops 114 engage the bodily tissue. This configuration may be advantageous when the bodily tissue is relatively inflexible and/or the passageway thereof has a relatively large open diameter. When in this configuration, the catheter 102 and the coiled engagement member 106 are preferably simultaneously advanced into the bodily lumen. Although it is generally only necessary to rotate the coiled engagement member 106 during advancement and engagement of the system 102, the catheter 102 may likewise be rotated simultaneously with the coiled engagement member 106.

FIG. 10B illustrates a second configuration for the system 100 wherein the loops 114 of the coil 108 are disposed distally of the distal end of the catheter 102. This configuration provides flexibility to the coil 108, and allows the coil 108 to bend or collapse as it is rotated or screwed into engagement with the inner surface of the bodily lumen. This configuration also allows the unsupported portion of the shaft 110 to curve or bend, thereby allowing the coil 108 to enter the bodily lumen along a pathway that is offset from or angled relative to the longitudinal axis of the catheter 102. This configuration may be advantageous when the passageway of the bodily tissue has a relatively small open diameter or is disposed at an obtuse angle. When in this configuration, the coiled engagement member 106 is typically rotated and advanced into the bodily lumen while maintaining the catheter 102 stationary. However, the catheter 102 may be advanced over the shaft 110 of the coiled engagement member 106 during advancement and engagement of the system 102 so as to straighten or provide additional support thereto.

Although the system 100 shown in FIGS. 10A and 10B comprise a pair of loops 114 having a substantially constant radius relative to the longitudinal axis of the shaft 110, other embodiments are contemplated. FIGS. 11A-11C illustrate several exemplary embodiments of a coiled engagement member having alternative coil configurations. Each of these alternative coil configurations may be advantageous for engaging and cannulating particular bodily lumens having different anatomical configurations. FIG. 11A illustrates a coiled engagement member 120 having four loops 122 with a radius that increases in the proximal direction so as to form a conical shaped coil 124. The coiled engagement member 120 may be particularly suited for accessing a bodily lumen having a very small diameter opening.

FIG. 11B illustrates a coiled engagement member 130 having three loops 132 with a radius that decrease in the proximal direction so as to form a reverse conical shaped coil 134. In addition, the end 136 of the wire is not connected to the proximal-most loop 132, but instead wraps closely about the shaft 138. The unconnected end 136 allows the coiled engagement member 130 to be pulled into and through the lumen of the catheter, thereby allowing removal of the coiled engagement member 130 therefrom once the catheter has gained access through the bodily lumen. This has the advantage of allowing another device, such as standard wire guide, to be advance through the lumen of the catheter.

FIG. 11C illustrates a coiled engagement member 140 having four loops 142 with a variable radius. Specifically, the radius increases from each end of the coil 144 towards the middle thereof. The resulting shape of the coil 144 is spindle or football shaped.

Figure 12:
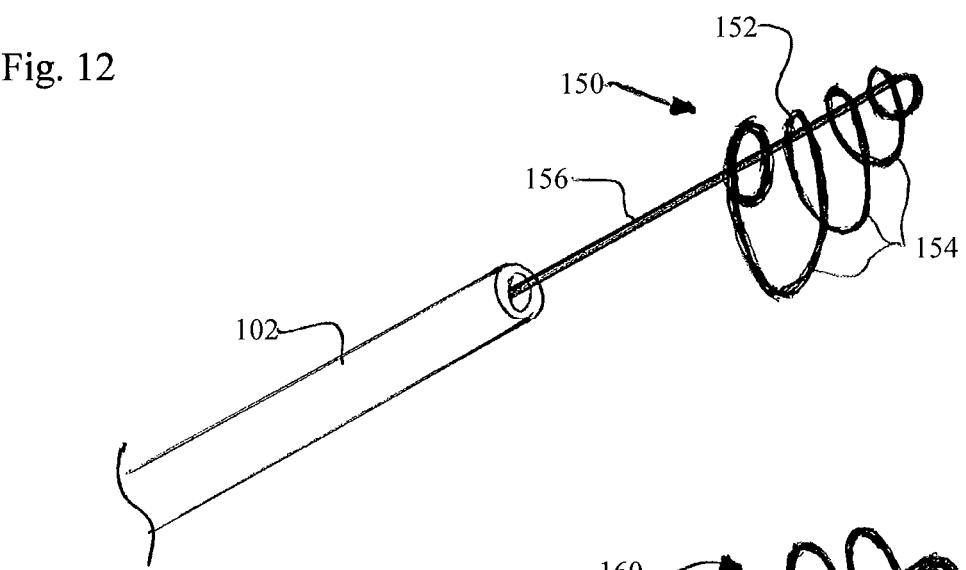
FIG. 12 shows another alternative embodiment of a coiled member having an eccentric profile according to the present invention.

FIG. 12 illustrates another embodiment of a coiled engagement member 150 having an offset or eccentric coil 152. In the particular embodiment illustrated, the loops 154 of the coil 152 have a constant radius along one side of the shaft 156, and an increasing (in the proximal direction) radius along the opposite side of the shaft 156. As a result, each of the loops 154 has a center that is offset from the longitudinal axis of the shaft 156, with the proximal-most loop 154 being the largest and most offset from the axis. Although the particular embodiment illustrated has generally circular shaped loops 154, the loops 154 may be non-circular in shape. The eccentric configuration of the coil 152 may advantageously allow selective cannulation of bifurcated bodily lumens or ducts. For example, the eccentric coil 152 may facilitate access into one or the other of the common bile ducts or the pancreatic duct. Specifically, once the coil 152 has been engaged within the ampullae, further rotation of the coiled engagement member 150 will cause the shaft 156 to be offset relative to the center of the ampullae, i.e., offset to a particular side of the ampullae passageway. This will in turn offset the longitudinal axis of the catheter 102 relative to the ampullae. This offset can then be used to orient or align the catheter 102 towards a particular duct, such as the pancreatic duct. The oriented catheter 102 can also be used to guide another device, such as a standard wire guide, into the desired duct. In a typical ERCP procedure, the apogee of the coil 152 is positioned within the ampullae at 3 o'clock to orient the catheter 102 towards the pancreatic duct, and at 11 o'clock to orient the catheter 102 towards the common bile duct.

In addition to orienting the catheter 102 within the ampullae, the eccentric coil 152 of the coiled engagement member 150 may be used to apply an eccentric pulling force to the ampullae. As the shaft 156 is pulled proximally to smooth the inter-mural mucosa of the ampullae, the eccentrically applied force of the shaft 156 may tend to shift or re-orient the passageway of the ampullae. This shifting may facilitate the passage of the catheter 102 through the ampullae, particularly if the longitudinal axis of the catheter 102 is at an obtuse angle relative to the passageway of the ampullae.

Figure 13:
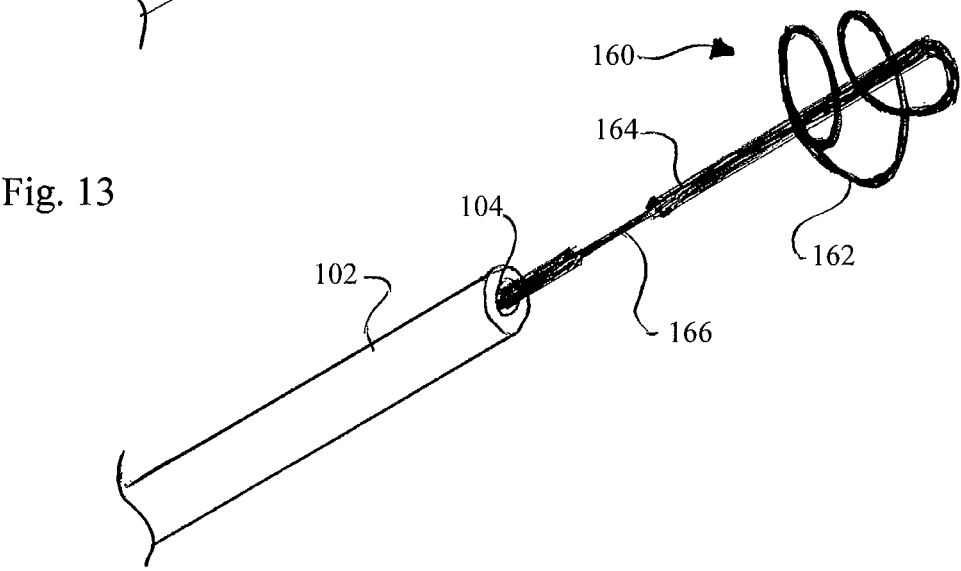
FIG. 13 shows another alternative embodiment of the a coiled member having a variable shaft flexibility according to the present invention.

FIG. 13 illustrates another embodiment of a coiled engagement member 160 having a shaft 162 with variable flexibility. In particular, the shaft 164 includes a reduced diameter section 166 that is configured to promote bending thereof. This configuration may be advantageous when attempting to engage the coil 162 with a bodily lumen having a passageway axis that is significantly angled relative to the longitudinal axis of the catheter 102. For example, as the coil 162 engages and is advanced into the bodily lumen, the natural channel of passageway of the bodily lumen may force the coil 162 and shaft 164 along a pathway that is angled relative to the catheter 102. The reduced diameter section 166 of the shaft 164 facilitates this angled pathway. Once the coil 162 has been fully engaged within the bodily lumen, the catheter 102 may then be advanced over the shaft 164 a sufficient distance until the reduce diameter section 166 is disposed within the lumen 104 of the catheter 102. As the reduced diameter section 166 passes into the lumen 104 of the catheter 102, the longitudinal axis of the catheter 102 will tend to align with the longitudinal axis of the shaft 164 of the coiled engagement member 160, as well as with the passageway of the bodily lumen.

In the particular embodiment illustrated in FIG. 13, the increased flexibility of the shaft 164 is provided by a reduced diameter section 166. However, the increased flexibility could be provided by using a different material or different structure. For example, increased flexibility could be provided by incorporating a coiled section into an intermediate portion of the shaft 164. The coiled section could also extend along a greater length of the shaft 164, although sufficient axial and torsional rigidity of the shaft 164 should still be maintained.

Figure 14:
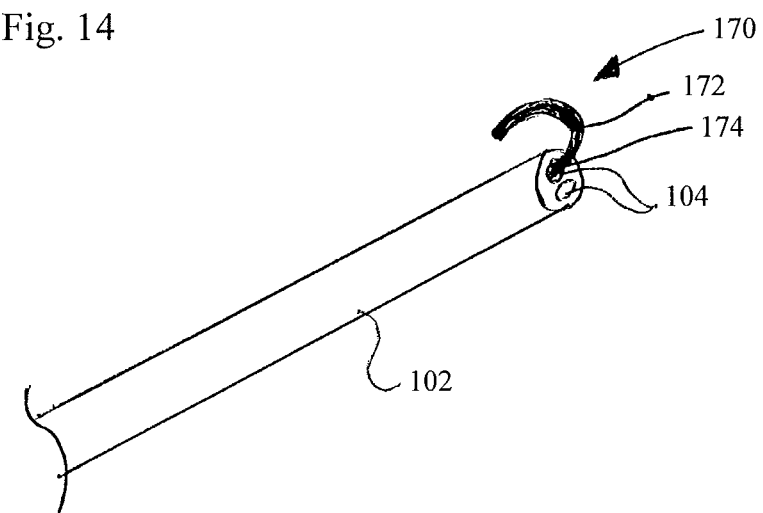
FIG. 14 shows a system including a hooked member according to an embodiment of the present invention.

FIG. 14 shows another embodiment according to present invention. This embodiment utilizes a hooked engagement member 170 having a hook 172 affixed to the distal end of an elongate shaft 174. The hook 172 comprises a curved wire that extends outwardly and proximally from the distal end of the shaft 174. The shaft 174 of the hooked engagement member 170 is shown extending through a lumen 104 of a multi-lumen catheter 102. The hook 172 is configured to engage and be secured to bodily tissue, such as the inner rim of the ampullae. The end of the hook 172 may be sufficiently sharp so as to securely attach to, for example, the inter-mural mucosa, or may be sufficiently blunt so as to prevent the hook 172 from causing excessive trauma to the engaged tissue.

The hooked engagement member 170 may be advantageous in engaging, retracting and smoothing any wrinkles of the ampullae without obstructing passage there through. In other words, the hook 172 presents a minimal profile that will be less likely to inhibit the passage of other elongate medical devices through the catheter 102. The hooked engagement member 170 may also be advantageous in permitting an eccentric pulling force to be applied to the bodily structure. The hooked engagement member 170 may also be easily retracted into and through the lumen 104 of the catheter 102, and subsequently removed there from.

Figure 15:
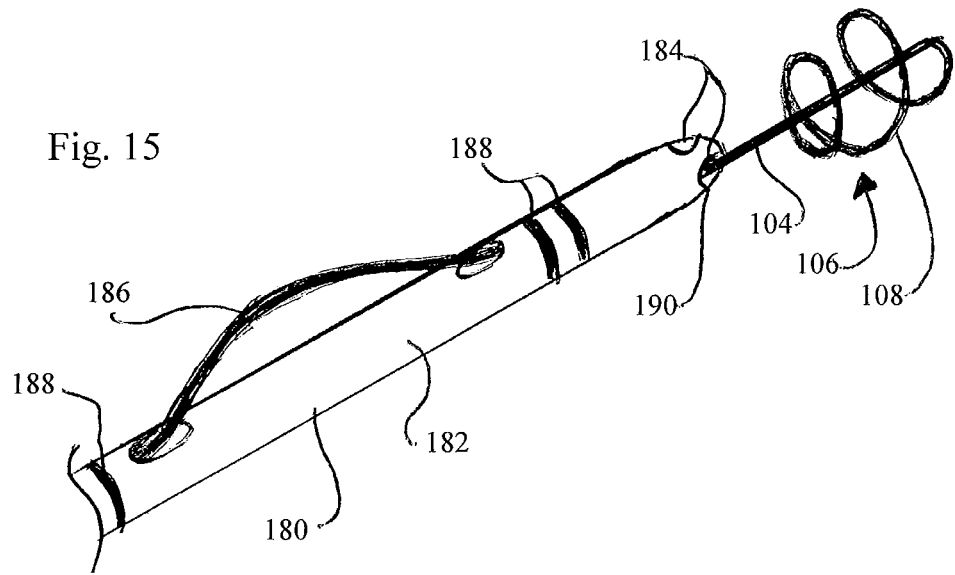
FIG. 15 shows a system including a sphincterotome and a coiled member according to an embodiment of the present invention.

FIG. 15 illustrates a coiled engagement member 106 of the type shown in FIGS. 10A and 10B in combination with a multi-lumen sphincterotome 180. The sphincterotome 180 is of conventional design and includes an elongate shaft 182 and a plurality of lumens 184. An electrosurgical cutting wire 186 extends outwardly from the catheter shaft 182 along the distal portion thereof. Radiopaque and/or visual markers 188 may be circumferentially about the catheter shaft 182 near each end of the cutting wire 186. The sphincterotome 180 also comprises a handle (not shown) attached to the proximal end of the catheter shaft 182, which is operably connected to the cutting wire 186. The handle also includes ports in communication with each of the lumens 184, and through which the shaft 104 of the coiled engagement member 106 may be advanced. In the particular embodiment illustrated, the distal end 190 of the catheter shaft 182 may be rounded or dome-shaped. Although not illustrated, the coil 108 may comprise a shape that is complimentary with the dome-shaped end 190 so as to be supported thereby during engagement of the bodily tissue. Other than the functional and structural differences between the sphincterotome 180 and the catheter 102 described above in connection with FIGS. 10A and 10B, the use of the coiled engagement member 106 to gain access to a bodily structure is essentially the same. In other words, the coiled engagement member 106, as well as the other embodiments described above, will function with any variety of elongate medical catheters.

Figure 16A:
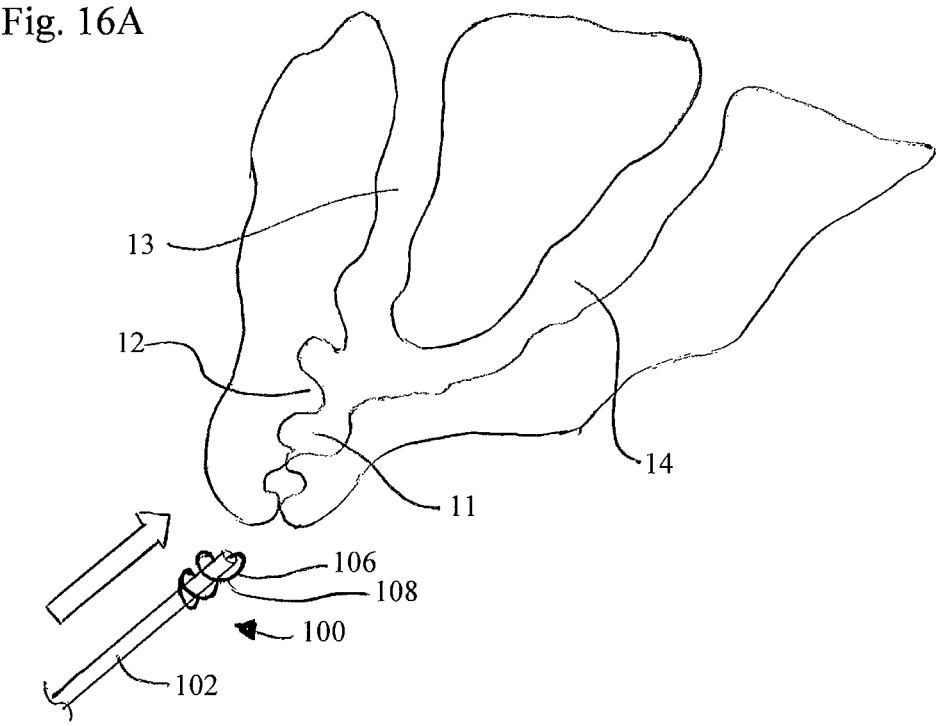
FIGS. 16A and 16B show a method of for using the system of FIGS. 10A and 10B to flatten out wrinkles within the inter-mural mucosa of the ampullae and align the passageway thereof with the longitudinal axis of the catheter.
Figure 16B:
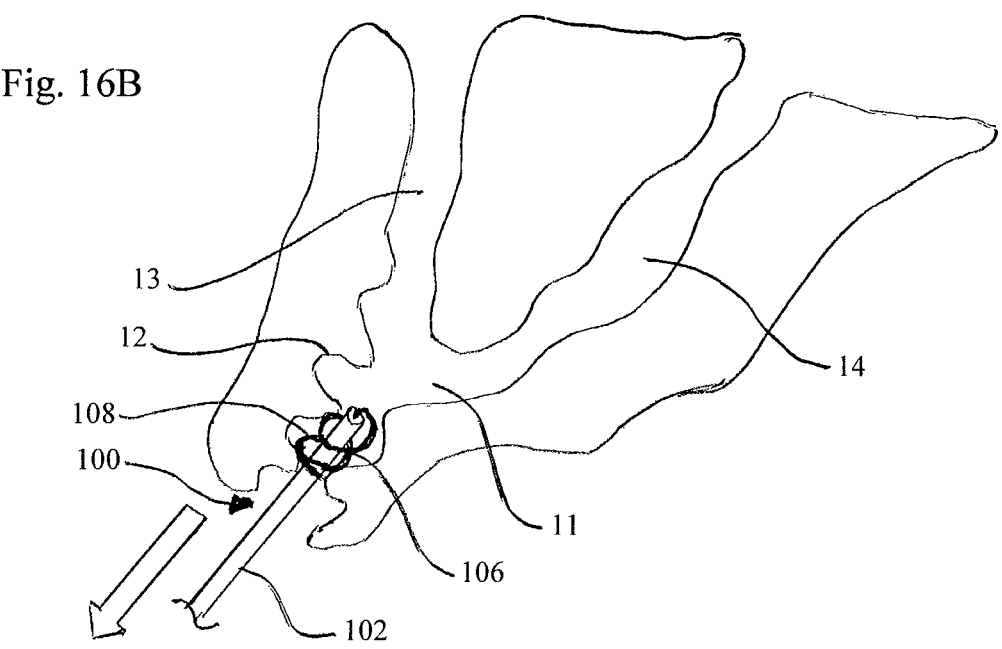

FIGS. 16A and 16B illustrate an exemplary method of using the system 100 of FIGS. 10A and 10B to gain access to the ampullae 11. In FIG. 16A, the catheter 102 and the coiled engagement member 106 of the system 100 are advanced simultaneously towards the ampullae 11 until it engages with the internal passageway thereof. This is accomplished by first contacting the coil 108 with the inner surface of the bodily lumen, and then rotating the coil 108 so as to advance the coil into the passageway of the ampullae 11 via a screw-in type of action. In particular, rotation of the coiled engagement member 106 causes the coil 108 to engage and advance along the folds 12 or other surface features of the inter-mural mucosa.

As illustrated in FIG. 16A, the longitudinal axis of the catheter 102 may be angled relative to the natural passageway of the ampullae 11 prior to engagement therewith. If the angle is significant, then it may be necessary to advance the coiled engagement member 106 distally relative to the catheter 10 to allow the shaft 110 of the coiled engagement member 106 to flex and follow the passageway of the ampullae 11.

As illustrated in FIG. 16B, once the coil 108 is fully engaged with the inter-mural mucosa of the ampullae 11, the coiled engagement member 106 can be used to align the longitudinal axis of the catheter 102 with the passageway of the ampullae 11, the common bile ducts 13, or the pancreatic duct 14. This may be accomplished by retracting or pulling the shaft 110 of the coiled engagement member 106 in a proximal direction so as to apply a proximal traction force to the ampullae 11. If the coiled engagement member 106 had been advanced distally of the catheter 102 during the initial engagement of the ampullae by the coil 108, then the catheter 102 should be advanced distally over the shaft 110 of the coiled engagement member 106 until the distal end of the catheter 102 engages the coil 108, as shown in FIG. 16B. This distal advancement of the catheter 102 over the shaft 110 of the coiled engagement member 106 will likewise tend to align the longitudinal axis of the catheter 102 with the passageway of the ampullae 11. Further traction applied to the ampullae 11 by the coiled engagement member 106 will tend to smooth out the wrinkles and flatten any folds 12 within the inter-mural mucosa of the ampullae 11, as shown in FIG. 4C.

The above specific embodiments are illustrative, and many variations can be introduced on these embodiments without departing from the spirit of the disclosure or from the scope of the appended claims. For example, elements and/or features of different illustrative embodiments may be combined with each other and/or substituted for each other within the scope of this disclosure and appended claims.

What is claimed is:

1. A medical system for gaining access into a bodily lumen or stricture, the system comprising:
    an elongate catheter extending along a longitudinal axis from a proximal end to a distal end, the distal end having an outer diameter, and a lumen extending through the catheter; and
    a coiled engagement member comprising an elongate shaft and a coil fixedly attached to a distal end of the elongate shaft, the elongate shaft being movably disposed within the lumen of the catheter, the coil being disposed near the distal end of the catheter,
    wherein the elongate shaft has sufficient torsional rigidity to transmit rotational motion from a proximal end of the elongate shaft to the coil;
    wherein the coil comprises a wire that curves outwardly and proximally from the distal end of the elongate shaft to form a plurality of loops circumferentially disposed about the distal end of the elongate shaft and forming a spiral shape around the elongate shaft, the plurality of loops being configured to engage an inner tissue surface of a bodily lumen or stricture;
    wherein an end of the wire is attached to a proximal-most loop of the plurality of loops,
    wherein a diameter of an opening defined by the proximal-most loop is wider than the outer diameter of the distal end of the elongate catheter, and
    wherein the system comprises a first configuration in which the plurality of loops are disposed circumferentially about the distal end of the catheter, and a second configuration in which the plurality of loops are disposed distally of the distal end of the catheter.

2. The medical system according to claim 1 wherein, in the first configuration, the coil is disposed about the catheter with a proximal end of the coil being spaced proximally from the distal end of the catheter.

3. The medical system according to claim 1 wherein, in the second configuration, the coil is disposed distally of the catheter with a proximal end of the coil being spaced distally of the distal end of the catheter.

4. The medical system according to claim 1 wherein the coil comprises a variable radius along a length thereof.

5. The medical system according to claim 1 wherein the wire of the coil is curvilinear and extends between a first end and a second end, the curvilinear wire having an intermediate portion forming a first loop and a second loop, the first end being integrally connected to the distal end of the elongate shaft, and the second end being affixed to the intermediate portion of the curvilinear wire.

6. The medical system according to claim 5 wherein the first loop and the second loop are approximately equal in size.

7. The medical system according to claim 5 wherein the first loop is larger than the second loop.

8. The medical system according to claim 5 wherein the first loop is smaller than the second loop.

9. The medical system according to claim 1 wherein the elongate shaft comprises a distal shaft section and an intermediate shaft section, the intermediate shaft section having a lateral flexibility that is greater than that of the distal shaft section.

10. The medical system according to claim 1 wherein the coil is eccentrically disposed relative to an axis of the elongate shaft.

11. The medical system according to claim 1 wherein the coil is re-configurable to a collapsed configuration having an outer diameter sufficiently small to pass through the lumen of the catheter.

12. The medical system according to claim 1 wherein the elongate catheter comprises a plurality of lumens extending therethrough.

13. The medical system according to claim 1 wherein the elongate catheter comprises a sphincterotome having an electrosurgical cutting wire disposed near the distal end thereof.

14. A method for gaining access into a bodily lumen or stricture, the method comprising the steps of:
    providing a system according to claim 1, and advancing the system to a target bodily lumen;

engaging the coil of the coiled engagement member with an inner surface of the target bodily lumen;

rotating the coil so as to advance the coil in a screw-like manner into a passageway of the target bodily lumen and secure the coil there within; and retracting the coil in a generally proximal direction so as to one of smooth the inner surface of the target bodily lumen and align the passageway of the target bodily lumen with the longitudinal axis of the catheter.

15. The method of claim 14 further comprising the step of advancing the elongate catheter into the passageway of the target bodily lumen.

16. The method of claim 14 further comprising the step of advancing an elongate shaft guide through the lumen of the elongate catheter and into the passageway of the target bodily lumen.

17. The method of claim 14 wherein the target bodily lumen comprises an ampullae, the inner surface comprises inter-mural mucosa, and the passageway comprises the sphincter of oddi.

* * * * *